United States Patent [19]

Pfänder et al.

[11] Patent Number: 4,728,934
[45] Date of Patent: Mar. 1, 1988

[54] TACTILE STIMULATION DEVICE FOR HEARING-IMPAIRED INDIVIDUALS

[75] Inventors: Wilhelm Pfänder, Sachsen; Friedrich Harless, Nuremburg; Horst Ruckdeschel; Dieter Busch, both of Forchheim, all of Fed. Rep. of Germany

[73] Assignee: Siemens Aktiengesellschaft, Berlin and Munich, Fed. Rep. of Germany

[21] Appl. No.: 922,832

[22] Filed: Oct. 23, 1986

Related U.S. Application Data

[63] Continuation of Ser. No. 471,644, Mar. 3, 1983, abandoned.

[30] Foreign Application Priority Data

Mar. 10, 1982 [DE] Fed. Rep. of Germany ....... 3208678

[51] Int. Cl.⁴ ..................... H04R 25/00; G09B 21/00
[52] U.S. Cl. ..................... 340/407; 381/68; 434/112; 434/114
[58] Field of Search ............. 340/407, 384 R, 521, 340/311.1; 179/107 BC, 107 R, 107 FD; 455/31; 310/30; 434/112, 114; 128/41; 381/68

[56] References Cited

U.S. PATENT DOCUMENTS

| | | | |
|---|---|---|---|
| 3,984,708 | 10/1976 | Holmlund et al. | 340/407 X |
| 4,139,742 | 2/1979 | Walker | 340/407 X |
| 4,225,965 | 9/1980 | Baugh | 340/407 X |
| 4,368,459 | 1/1983 | Sapora | 340/407 |

FOREIGN PATENT DOCUMENTS 2044977A 10/1980 United Kingdom ............... 434/112

OTHER PUBLICATIONS

"A New Way of Hearing", Washington Star, Mar. 20, 1972, Judith Randal.
"Tactile Speech Simulator to Aid Deaf", Barry Gross Washington Business, Washington Post, 10-11-82, p. 5.
*Systemerganzte Artikulation*, published by Julius Groos Verlag, Heidelberg, 1980, pp. 58, 61 and 64.

Primary Examiner—James L. Rowland
Assistant Examiner—Brent A. Swarthout
Attorney, Agent, or Firm—Hill, Van Santen, Steadman & Simpson

[57] ABSTRACT

An electro-acoustical transmitter converts electrical signals which correspond to acoustical events into mechanical vibrations which are transmitted onto the skin. The aim is to achieve a small vibrator which, insofar as possible, can be worn on the wrist, for instance, in the manner of a wristwatch. To that end, a coil is employed into which a magnetic core, resiliently mounted relative thereto for instance by a diaphragm, projects as an armature. The housing which carries both the diaphragm and the coil forms the magnetic return flux path. Thus, a miniaturization of the vibrator on the desired order is achieved. An inventive vibrator is particularly suited for the deaf.

5 Claims, 2 Drawing Figures

TACTILE STIMULATION DEVICE FOR HEARING-IMPAIRED INDIVIDUALS

This is a continuation of application Ser. No. 471,644, filed Mar. 3, 1983, now abandoned.

BACKGROUND OF THE INVENTION

The invention relates to a speech information transmission device for the tactile transmission of speech information so as to be suitable for persons having severe hearing impairment. Such a device comprises a tactile stimulation unit and produces mechanical vibrations. Such devices are known, for example, from pages 57 through 67 of the book "Systemergänzt Artikulation" by K. Schulte et al, published in 1980 by the Julius Groos Verlag, Heidelberg.

Devices of the above type, as known, are particularly employed for persons having severe hearing impairment because a good sensory perception can be developed from the mechanical vibrations produced thereby. It has been shown that a favorable disposition of a transmitter for producing such vibrations is particularly in the area of the wrist. This leads to the conclusion that, in comparison to previous devices, one would like to have smaller tactile stimulation units which could be worn, for instance, in the manner of a wrist watch.

SUMMARY OF THE INVENTION

The object of the invention is therefore to provide a tactile stimulation unit of the type suitable for persons having a severe hearing impairment wherein the unit is of a configuration adapted to be worn on the wrist and has substantially a minimum height dimension. This object is realized in preferred implementations of the invention by a housing of magnetic material providing a return flux path at one axial end and along the exterior of the electric coil, the vibration transmitter and movable magnetic core being resiliently mounted, and the movable magnetic core occupying substantially the entire axial extent of the central interior region of the electric coil. In an illustrated preferred implementation, a minimum height of the wrist-worn device is achieved since the axial extent of the coil and the axial extent of the movable magnetic core are substantially coextensive. Also in an illustrated embodiment, the housing is cup-shaped and has an integral interior cylindrical wall of magnetic material encircling the electric coil and coextensive with the axial extent of the electric coil, with a diaphragm extending across the open end of the housing and providing the resilient mounting of the vibration transmitter and movable magnetic core.

Previous construction of vibrators is based on the thought that one would like to transmit as wide as possible a frequency band in order to achieve conditions corresponding to normal acoustics even given this type of transmitting of acoustic events. This, however, requires the known configuration which primarily derives from a desire that the armature of the vibration transmitter should exhibit an air gap relative to the electromagnet, said air gap lying approximately in the center of the coil. However, an overall minimum height of the vibration transmitter is thus required so that both the armature as well as the electromagnetic core can project into the coil. When these conditions are not observed, then one must expect the occurrence of undesired phenomena, particularly eddy currents which at least have a negative effect on the transmission of higher frequencies.

In contrast thereto, the invention proceeds on the basis that the sense of touch of the skin for vibrations greatly decreases anyway above one kilohertz (1 kHz). This led to the concept of restructuring the armature of the vibration transmitter and the core of the electromagnet. As a result, the overall height of the magnetic circuit can be reduced and a significant miniaturization of the vibrator can be achieved. Surprisingly, no significant loss of transmitted sensation occurs in comparison to the known, relatively large vibrators even though in the inventive vibrator the space requirements have been reduced to approximately one-fourth.

The inventive miniaturization of a vibrator is achieved in that, with the employment of a vibrating central core part instead of the standard toroidal electromagnet, the diameter can be reduced to less than half and that the thickness can also be reduced when the large diameter armature is eliminated. Moreover, the space requirement can be reduced according to the invention in that the return magnetic flux path external of the coil is provided by the housing itself. To that end, the housing need merely be manufactured of magnetic material, for example, of steel. Thus, a significant miniaturization of the vibrator can be achieved in comparison to a thickness of at least 2 cm and a diameter of 5 cm in the known execution, the miniaturized vibrator according to the present invention then being suitable for fastening to a wrist band because snagging on the vibrator or, respectively, its stripping from the arm are largely prevented. In addition to being suitable for training individual deaf persons, this also makes it suitable for employment with hearing training devices for a plurality of trainees, so-called aural-oral systems for the simultaneous instruction of a plurality of trainees.

It has further proven favorable for wearing in the manner of a wristwatch to insert the actual vibrator in a synthetic part which can in turn be designed as a connection to a wrist strap. The inventive surprisingly great miniaturization allows a connection with a standard wristwatch strap.

The line conducted to the vibrator for the electrical signals can be attached strain-relieved without requiring an additional space in that an entrance passage is left free between the outer wall of the housing and the support part receiving the wrist strap, the line being wound around an interior wall of magnetic material spaced inwardly of the outer wall. Even one turn between the introduction of the line into the housing and its connection to the coil offers protection against break-away. Two turns have produced a good compromise between improved strain-relief and space requirements.

Further details and advantages of the invention are explained on the basis of the exemplary embodiments illustrated on the attached drawing sheet; and other objects, features and advantages will be apparent from this detailed disclosure and from the appended claims.

DETAILED DESCRIPTION

Figure 1:
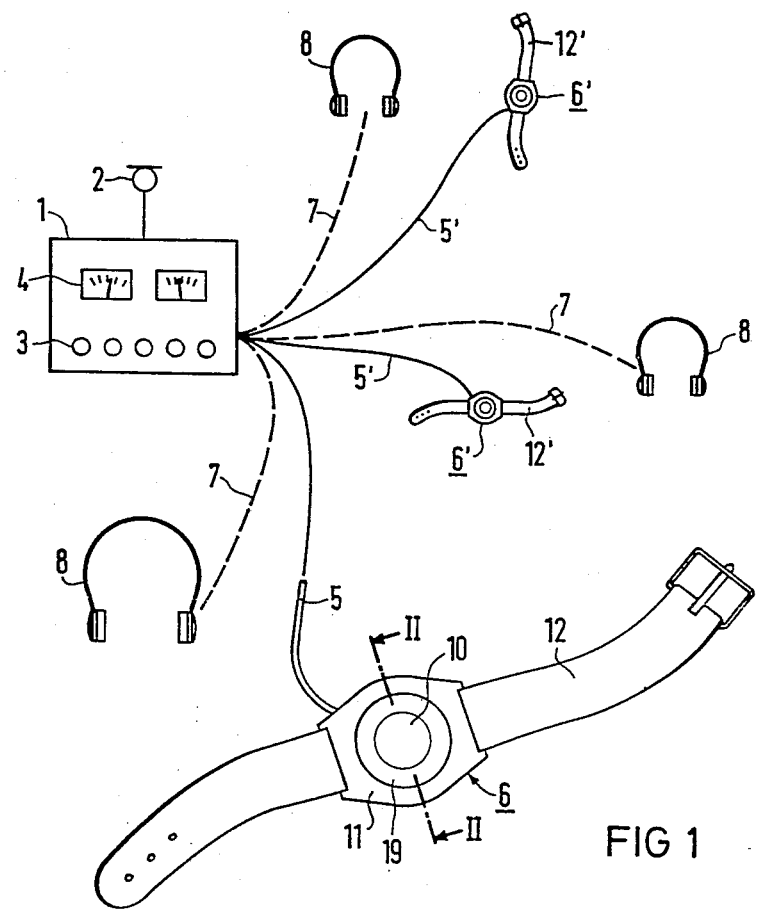
FIG. 1 shows a schematic illustration of a device which can be provided with one or, respectively, a plurality of vibrators inventively designed in the manner of a wristwatch.
Figure 2:
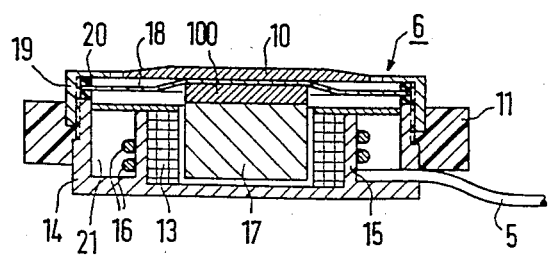
FIG. 2 shows a cross-section through an inventively designed vibrator, the section being taken along the line II—II of FIG. 1.

Referenced in FIG. 1 with 1 is a device in which amplified electric signals are produced. Such signals may originate from acoustic signals which are picked up in a microphone 2, or, respectively, which derive from other signal sources (radio, television, tape recorder, etc.). The electric signals, after adjustment which is indicated by means of adjustment knobs 3 and display elements 4, are then transmitted over a line 5 to a vibrator 6. At the same time, however, further connections to the lines 5' and vibrators 6' can also be provided. Head sets 8 can also be connected over further lines indicated at 7. In its center, the vibrator 6 contains the actual vibration transmitter 10. This is mounted for axial vibration centrally of a support 11 consisting of synthetic material. The support 11 has suitable means for receiving a wristwatch strap 12 which can serve for fastening the vibrator 6 to the wrist, so as to hold the vibration transmitter 10 in contact with the wrist.

The vibrator 6 includes a coil 13 which is disposed in a housing 14. A magnetic core 17 is situated longitudinally movable in the opening of the coil 13, said magnetic core 17 being secured to the signal transmitter 10 at its surface located toward the open side of the coil. This transmitter 10 moreover, is supported at a diaphragm 18 which also supports through a connecting region 100 the magnetic core 17 inside the coil 13. The diaphragm 18 and, thus, the transmitter 10 together with the magnetic core 17 are fixed to the housing 14 by means of an internally threaded coupling ring 19, whereby the edge of the diaphragm 18 lies in an elastic support 20 consisting of synthetic material. As can be seen from the cross-sections of two turns 16, the line 5 is conducted around the wall 15 of housing 14 and is disposed in an annular recess 21 of the housing 14, said wall 15 surrounding the coil 13. Thus, a pull on the cable 5 only influences the winding 16 around the wall 15 of the housing which surrounds the coil 13, but such a pull prevents tearing away the electrical connection of the cable 5 with the coil 13.

It will be apparent that many modifications and variations may be made without departing from the scope of the teachings and concepts of the present invention.

We claim as our invention:

1. A speech information transmission device for tactile transmission via vibrations from a vibration transmitter indicative of speech information, comprising:
    a wrist-watch shaped housing;
    an electric coil received within the housing;
    a magnetic core movably received within a central region of the electric coil and longitudinally movable in the coil;
    a portion of the housing being substantially cup-shaped for receiving the coil and the core, the housing surrounding the coil providing a flux return path for flux lines passing through the core;
    one end of the core being adjacent the bottom of the housing at one end of the coil and the opposite end of the core terminating at the opposite end of the coil so that the core does not project beyond either end of the coil;
    a diaphragm securely connected to the core and having a peripheral edge secured to the housing; and
    a vibration transmitter element independently movable with respect to the housing and supported by the diaphragm, said diaphragm retaining both the transmitter element and the magnetic core such that they are both freely oscillatable.

2. A speech information transmission device for tactile transmission via vibrations from a vibration transmitter indicative of speech information, comprising:
    a wrist-watch shaped housing;
    an electric coil received within the housing;
    a magnetic core movably received within a central region of the electric coil and longitudinally movable in the coil;
    a portion of the housing being substantially cup-shaped for receiving the coil and the core, the housing surrounding the coil providing a flux return path for flux lines passing through the core;
    one end of the core being adjacent the bottom of the housing at one end of the coil and the opposite end of the core terminating at the opposite end of the coil so that the core does not project beyond either end of the coil;
    a diaphragm securely connected to one end of the core and having a peripheral edge secured to the housing; and
    a vibration transmitter element independently movable with respect to the housing and attached centrally to the diaphragm at a side opposite to which the magnetic core is secured, said diaphragm retaining both the transmitter element and the magnetic core such that they are both freely oscillatable.

3. A device according to claim 2 wherein the housing has a wrist-watch configuration with an upper opening and wherein the resilient diaphragm is attached at the upper opening such that the vibration transmitter element is positioned at the opening.

4. A device according to claim 2 wherein the peripheral edge of the diaphragm is attached via an elastic support of synthetic material to the housing.

5. A device according to claim 4 wherein a coupling ring attaches the elastic support to outer side walls of the housing.

* * * * *